United States Patent [19]
Dazai et al.

[11] 3,952,011
[45] Apr. 20, 1976

[54] PROCESS FOR PRODUCING HEMI-ALKALI METAL SALT OF 2-PYRROLIDONE-5-CARBOXYLIC ACID

[75] Inventors: Miyoji Dazai, Yokkaichi; Katsumi Sugiyama, Kawasaki; Masaaki Iida, Yokohama; Hideo Tazuke, Tokyo; Hiroo Kageyama, Kamakura, all of Japan

[73] Assignee: Ajinomoto Company, Ltd., Tokyo, Japan

[22] Filed: Feb. 25, 1974

[21] Appl. No.: 445,771

Related U.S. Application Data

[63] Continuation of Ser. No. 206,165, Dec. 8, 1971, abandoned.

[52] U.S. Cl. .......................................... 260/326.45
[51] Int. Cl.² ........................................ C07D 207/28
[58] Field of Search .............................. 260/326.45

[56] References Cited
FOREIGN PATENTS OR APPLICATIONS
82CAM  6/1965  France

Primary Examiner—Richard J. Gallagher
Assistant Examiner—Mark L. Berch
Attorney, Agent, or Firm—Oblon, Fisher, Spivak, McClelland & Maier

[57] ABSTRACT

Hemi-alkali metal salts of 2-pyrrolidone-5-carboxylic acid, believed to have the formula:

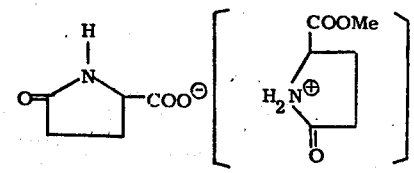

wherein Me is an alkali metal, is formed by reaction of 0.75 to 0.99 moles of an alkali metal hydroxide per mole of 2-pyrrolidone-5-carboxylic acid.

9 Claims, No Drawings

PROCESS FOR PRODUCING HEMI-ALKALI METAL SALT OF 2-PYRROLIDONE-5-CARBOXYLIC ACID

CROSS REFERENCE TO RELATED APPLICATIONS

This is a continuation of application Ser. No. 206,165, filed Dec. 8, 1971, now abandoned.

BACKGROUND OF THE INVENTION

1. Field of the Invention

This invention relates to hemi-alkali metal salts of 2-pyrrolidone-5-carboxylic acid and to methods for producing the same.

2. Description of Prior Art

Although mono-alkali salts of 2-pyrrolidone-5-carboxylic acid are known, the hemi-alkali metal salts of 2-pyrrolidone-5-carboxylic acid (hereinafter abbreviated as PCA · ½ Me), as far as the present inventors are aware, is a novel compound which has never been disclosed in the available literature. The object is to produce PCA.½ salt industrially, which is useful in obtaining high purity PCA or the salt thereof which can be used as a material for medicine or cosmetics.

SUMMARY OF THE INVENTION

Accordingly, it is one object of this invention to provide the novel compounds indicated as hemi-alkali-salts of 2-pyrrolidone-5-carboxylic acid.

It is another object of this invention to provide a process for producing said novel compounds in an industrially acceptable manner.

These and other objects have now been attained by the discovery that the hemi-alkali salts of 2-pyrrolidone-5-carboxylic acid, represented by the formula:

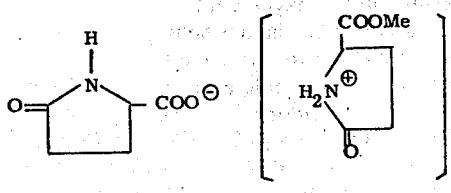

wherein Me is an alkali metal, can be produced by reacting an alkali metal hydroxide with 2-pyrrolidone-5-carboxylic acid in a mole ratio of 0.75 to 0.99 moles of alkali mtal hydroxide per mole of 2-pyrrolidone-5-carboxylic acid.

DETAILED DESCRIPTION OF THE INVENTION

It has now been discovered that PCA . ½ Me, which consists of one molecule of an alkali metal and two molecules of 2-pyrrolidone-5-carboxylic acid (hereinafter referred to as "PCA") will exist independently only within the specified extent of mole ratio range of 0.75 to 0.99 moles of alkali metal hydroxide per mole of PCA. At lower mole ratios, PCA will co-exist with PCA . ½ Me, or will selectively exist to the exclusion of the PCA . ½ Me. At a higher mole ratio, the well known mono-alkali salt of PCA will exist so that pure PCA . ½ Me cannot be obtained.

It is most desirable to use a mole ratio in the middle domain of the above-recited range, i.e., 0.8 to 0.95, so as to avoid still further the poor results that will be obtained when the critical ratios are exceeded in either direction.

Suitable forms of PCA which may be used in this reaction include the DL-form and its optically active enantiomorphs. The various impurities or coloring materials which are often found in PCA will not disturb this reaction.

Suitable alkali metal hydroxides for this reaction include sodium hydroxide or potassium hydroxide.

In carrying out this reaction, the alkali metal hydroxide and the PCA, in the requisite amounts are admixed in an aqueous solvent. The precipitation obtained is then separated by any conventional means, such as filtration, or the metal washed and dried.

PCA . ½ Me has an excellent crystallization nature, in that it will crystallize out at a high velocity, and it will show good separation from the mother liquor, as compared with the separation obtained by mono-alkali metal salts of PCA crystallization. Moreover, the crystal growth will not be adversely affected by the presence of such usual impurities as colored materials or glutamic acid. Even in the presence of such impurites, crystallization will be even and will be of uniformly high purity.

As another differentiation from the corresponding mono-alkali metal salts, PCA . ½ Me is characterized by relatively low hygroscopicity, as compared with the mono-alkali salts.

These aspects of PCA . ½ Me therefore, make it a very industrially attractive substitute for PCA or for the mono-alkali metal salts of PCA, when a high purity compound is required.

The elementary analysis of PCA . ½ Me is as follows:

| (1) | Elemental analysis | | Found | Calculated |
|---|---|---|---|---|
| | PCA . ½Na | C: | 43.00% | 42.90% |
| | (Empirical formula: | H: | 4.79% | 4.66% |
| | $C_{10}H_{13}N_2O_6Na$) | N: | 10.07% | 10.00% |
| | | Na*: | 8.20% | 8.21% |
| (2) | Elemental analysis | | Found | Calculated |
| | L-PCA . ½K | C: | 40.50% | 40.53% |
| | (Empirical formula: | H: | 4.39% | 4.42% |
| | $C_{10}H_{13}N_2O_6K$) | N: | 9.38% | 9.45% |
| | | K*: | 13.22% | 13.20% |
| (3) | Elemental analysis | | Found | Calculated |
| | DL-PCA . ½K . ½$H_2O$ | C: | 38.19% | 38.21% |
| | (Empirical formula: | H: | 4.79% | 4.81% |
| | $C_{10}H_{15}N_2O_7K$) | N: | 8.93% | 8.91% |
| | | K*: | 12.48% | 12.44% |

*Elemental analysis of Na or K was by atomic absorption spectrophotometry.

The X-ray powder diffractiometric figure of PCA . ½ ME is quite different from that of PCA or equimolar mixtures of mono-alkali metal salts of PCA and PCA.

A dilute pure water solution of PCA . ½ Me will be acidic in pH. In order to separate PCA from PCA . ½Me in an aqueous solution, it is desirable to add a strong acid and to contact the mixture with an ion-exchange resin in order to reduce the effective amount of alkali metal to assure that the mole ratio is close to the above-specified range. PCA can also be easily separated by contact with a large quantity of water.

It is interesting to note that PCA . ½ Na does not possess water of crystallization in either its optically active enantiomorph or in its DL-form. It is also interesting to note, as being quite unusual, the fact that for PCA . ½K, water of crystallization exists in the case of the DL-form, but not in the case of its optically active enantiomorph.

Having now generally described the invention, a further understanding can be attained by reference to certain specific Examples which are provided herein for purposes of illustration only and are not intended to be limiting unless otherwise so specified.

EXAMPLE 1

250 ml. of water was added to 258 g. of DL-RCA crystals in order to prepare a slurry-like material. Sodium hydroxide crystals were added to this mixture, with caution to the release of neutralization heat. When 60 g. of sodium hydroxide was added, the solution turned perfectly transparent. However, when 65 g. of sodium hydroxide was added, a precipitation of the crystals was observed. After standing for one night, the crystals were separated by filtration, washed with methanol and ether, and dried.

Yield: 82 g.

Analysis: N : 10.05% (Kjeldahl method); Na: 8.18% (Atomic absorption spectrophotometric method).

EXAMPLE 2

93 g. of potassium hydroxide were added to the same amount of crystallization slurry of L-PCA. Insoluble materials were separated by filtration, and the filtrate was concentrated under reduced pressure and allowed to stand overnight. The precipitated crystals were separated by filtration, washed and dried.

Yield: 127 g.

Analysis: N : 9.41%; K : 13.2% (Atomic absorption spectrophotometric method).

EXAMPLE 3

129 g. of brown-colored DL-PCA which were produced from the hydrolysis of 5-(2-cyanoethyl)hydantoin, were suspended in 125 ml. of water. Sodium hydroxide crystals were gradually added to this mixture. When 30 g. of sodium hydroxide were added, the solution appeared homogeneous, but, when the mixture was cooled after the addition of 35 g. sodium hydroxide, the precipitation of crystals was observed. After standing overnight, the crystals were separated by filtration, washed, and dried.

Yield: 45 g.

The coloration of the crystals was not entirely seen.

Analysis of sodium: 8.18%.

28 g. of these crystals were stirred into 100 g. of water for 1 hour and dissolved. The newly precipitated crystals were separated by filtration and dried.

Yield: 4.8 g.

Analysis of nitrogen: 10.81%.

This value is equivalent to the analysis of nitrogen in PCA.

In comparison, the brown-colored materials could not be removed from PCA, which was produced by recrystallization in hot water from brown-colored DL-PCA as mentioned above.

EXAMPLE 4

294.2 g of L-glutamic acid were suspended in 220 ml. of water and heated at 200°C. for 3 hours. This reaction mixture contained 21.8 g. of glutamic acid and was slightly colored. Sodium hydroxide crystals were added gradually to the reaction mixture, adjusted to pH 5 and air-cooled. The precipitated crystals were separated by filtration, washed and dried.

Yield: 35 g.

The said crystals are entirely colorless, showed the following analysis data, and were identified as the hemi-sodium salt of DL-PCA.

Analysis: N : 10.01% (Kjeldahl method); N : 0.00% (Van Slyke method); Na : 8.21% (Atomic absorption spectrophotometric method).

Having now fully described the invention, it will be readily understood by one of ordinary skill in the art that many changes and modifications can be made thereto without departing from the spirit or scope of the invention. ACCORDINGLY,

What is claimed and intended to be covered by letters patent is:

1. Hemi-alkali salt of 2-pyrrolidone-5-carboxylic acid.

2. The salt of claim 1, which is hemi-sodium salt of 2-pyrrolidone-5-carboxylic acid.

3. The salt of claim 2, which is hemi-sodium salt of DL-2-pyrrolidone-5-carboxylic acid.

4. The salt of claim 1, which is hemi-potassium salt of 2-pyrrolidone-5-carboxylic acid.

5. The salt of claim 4, which is hemi-potassium salt of L-2-pyrrolidone-5-carboxylic acid.

6. The salt of claim 4, which is hemi-potassium salt of DL-2-pyrrollidone-5-carboxylic acid · ½ $H_2O$.

7. A process for producing a crystalline hemi-alkali metal salt of 2-pyrrolidone-5-carboxlyic acid which comprises reacting an alkali metal hydroxide with 2-pyrrolidone-5-carboxylic acid in a mole ratio of 0.75 to 0.99 moles of alkali metal hydroxide per mole of 2-pyrrolidone-5-carboxylic acid.

8. The process of claim 7, wherein said reaction is carried out in an aqueous solution.

9. The salt of claim 2, which is the hemi-sodium salt of L-2-pyrrolidone-5-carboxylic acid.

\* \* \* \* \*